(12) United States Patent
Richardson

(10) Patent No.: US 6,783,573 B2
(45) Date of Patent: Aug. 31, 2004

(54) GAS SAMPLING SYSTEM

(75) Inventor: Peter Richardson, Beaverton, OR (US)

(73) Assignee: Welch Allyn Protocol, Inc., Beaverton, OR (US)

( * ) Notice: Subject to any disclaimer, the term of this patent is extended or adjusted under 35 U.S.C. 154(b) by 0 days.

(21) Appl. No.: 10/256,308

(22) Filed: Sep. 27, 2002

(65) Prior Publication Data

US 2004/0060443 A1 Apr. 1, 2004

(51) Int. Cl.[7] .............................. B01D 53/22; A62B 7/10
(52) U.S. Cl. .................................. 96/6; 96/111; 96/413; 55/DIG. 35; 128/205.27; 73/23.3
(58) Field of Search ......................... 128/205.27, 205.29, 128/206.11–206.19, 206.22, 207.14, 207.16, 207.18; 95/117; 96/4, 6, 108, 111, 413; 55/385.1, DIG. 35; 73/23.3; 34/79

(56) References Cited

U.S. PATENT DOCUMENTS

| | | | | |
|---|---|---|---|---|
| 4,327,718 A | * | 5/1982 | Cronenberg | ........... 128/205.12 |
| 4,446,869 A | * | 5/1984 | Knodle | ........................ 600/529 |
| 4,705,543 A | | 11/1987 | Kertzman | |
| 4,886,528 A | * | 12/1989 | Aaltonen et al. | ................. 96/6 |
| 5,042,500 A | * | 8/1991 | Norlien et al. | ............... 600/532 |
| 5,131,387 A | * | 7/1992 | French et al. | .......... 128/205.27 |
| 5,143,695 A | * | 9/1992 | van den Burg | ................ 422/84 |
| 5,233,996 A | * | 8/1993 | Coleman et al. | ....... 128/205.27 |
| 5,284,054 A | * | 2/1994 | Loebach | ...................... 73/23.3 |
| 5,616,158 A | * | 4/1997 | Biendarra et al. | .......... 96/117.5 |
| 6,346,142 B1 | * | 2/2002 | Jetter et al. | ....................... 96/9 |

* cited by examiner

Primary Examiner—Frank M. Lawrence
(74) Attorney, Agent, or Firm—Wall Marjama & Bilinski LLP

(57) ABSTRACT

The present invention is directed to a gas sampling system for conducting respiratory gases from a patient respiratory gas output mechanism to a respiratory gas monitoring device. A gas sampling tube is coupled to an input connector. The gas sampling tube is configured to conduct the respiratory gases from the patient to the gas monitoring device. An output connector couples the gas sampling tube to the monitor input connector. An output dryer tube is coupled between the gas sampling tube and the output connector. The output dryer tube is characterized by a tube length and a relative moisture removal efficiency. The relative moisture removal efficiency is dependent on the tube length. The tube length is selected to limit the moisture content of the respiratory gasses being directed into the respiratory gas monitor to a predetermined level.

23 Claims, 1 Drawing Sheet

GAS SAMPLING SYSTEM

FIELD OF THE INVENTION

The present invention relates generally to the art of respiratory gas analysis, and particularly to a gas sampling system for conducting respiratory gases from a patient to a respiratory gas monitoring device.

BACKGROUND OF THE INVENTION

Respiratory gas monitoring is used extensively in medical and clinical settings. Gas monitors are an invaluable tool in providing care providers with information relating to a patient's metabolism. Medical personnel are often interested in the relative and absolute amounts of oxygen and carbon dioxide in the respired gases to determine a patient's respiratory function and oxygen metabolization. Respiratory gas monitoring is also important during surgery. Anesthesia must be carefully administered. An overdose of anesthesia, or a lack of oxygen, could lead to brain damage or death. On the other hand, if the anesthesiologist does not administer enough anesthesia the patient may become aware during the surgical procedure and experience severe pain and discomfort.

Respiratory gasses are delivered from a patient to the gas monitor by way of a gas sampling system. A patient's respiratory gasses are directed into the gas sampling system by a respiratory output device such as an oral/nasal cannula, a nasal cannula, an endotracheal tube, a tracheostomy tube, or a mask. The gases are conducted from the respiratory output device to the monitor by a connecting gas sampling tube. Gas monitors often display the inhaled and exhaled concentrations of oxygen ($O_2$), carbon dioxide ($CO_2$), nitrous oxide ($N_2O$), and/or anesthetic agents. Alarms are typically sounded when a gas concentration falls outside a predetermined range of values.

A common problem with the aforementioned gas sampling system relates to the $CO_2$ detector in the monitor. In addition to conducting respired gasses to the monitor, gas sampling tubes may also direct damaging moisture into the $CO_2$ detector. In one approach that has been considered, gas sampling systems were equipped with water trap and gas flow shut-off mechanisms. Typically, the valve mechanism is disposed in the connector coupling the gas sampling tube to the gas monitor. While the valve mechanism prevents water from damaging the $CO_2$ detector, it is also adapted to substantially restrict the flow of respiratory gasses if the valve is exposed to too much moisture. When this occurs, the gas sampling system must be replaced. In another approach that has been considered, the moisture problem has been addressed by placing a dryer mechanism in the connector adjacent to, or proximate to, the respiratory output device (e.g., the mask, cannula, or etc.). Unfortunately, this approach also has several drawbacks.

In one scenario, the patient is disposed in an incubator or in an oxygen tent, while the gas monitor is disposed downstream in a room-temperature environment. Of course, the environment in the oxygen tent or incubator is typically warmer and more humid than the room temperature environment. As the respired gasses propagate from the warmer environment to the room-temperature environment, condensate forms in the section of the gas sampling tube located in the room-temperature environment. Thus, the dryer mechanism disposed proximate the patient is ineffective, and the water trap shut-off valve located adjacent the gas monitor is quickly closed.

In another scenario, the patient is wearing a nasal cannula and is disposed in a cooler environment. When the patient exhales, the respired gas is at body temperature and saturated with water. Condensate typically forms in the cannula. The dyer mechanism disposed in the gas sampling tube adjacent to the cannula will remove some of the moisture. However, as the respiratory gasses propagate from the patient to the gas monitor, additional condensate will form in the gas sampling tube. Obviously, the dryer mechanism disposed near the patient cannot remove the additional condensate. Again, the water trap shut-off valve located adjacent the gas monitor will close in a relatively short period of time.

What is needed is a gas sampling system that is equipped to successfully remove condensate that forms along the entire length of the gas sampling tube. What is also desirable is a gas sampling system that substantially removes water before it is directed into the valve mechanism.

SUMMARY OF THE INVENTION

The gas sampling system of the present invention addresses the aforementioned problems. The gas sampling system of the present invention is equipped to remove condensate that forms along the entire length of the gas sampling tube. The present invention is configured to remove water in the respired gasses before the water is directed into the valve mechanism. In so doing, the gas sampling system of the present invention has an effective operational life-span that is far superior to the related systems described above.

One aspect of the present invention is a gas sampling system for conducting respiratory gases from a patient respiratory gas output mechanism to a respiratory gas monitoring device. The respiratory gas monitoring device is equipped with a monitor input connector. The gas sampling system includes an input connector configured to couple the gas sampling system to the patient respiratory gas output mechanism. A gas sampling tube is coupled to the input connector. The gas sampling tube is configured to conduct the respiratory gases from the patient to the gas monitoring device. An output connector couples the gas sampling tube to the monitor input connector. An output dryer tube is coupled between the gas sampling tube and the output connector. The output dryer tube is characterized by a tube length and a relative moisture removal efficiency. The relative moisture removal efficiency is dependent on the tube length. The tube length is selected to limit the moisture content of the respiratory gasses being directed into the respiratory gas monitor.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWING

For a further understanding of these and objects of the invention, reference will be made to the following detailed description of the invention which is to be read in connection with the accompanying drawings, wherein.

DETAILED DESCRIPTION OF THE INVENTION

Figure 1:
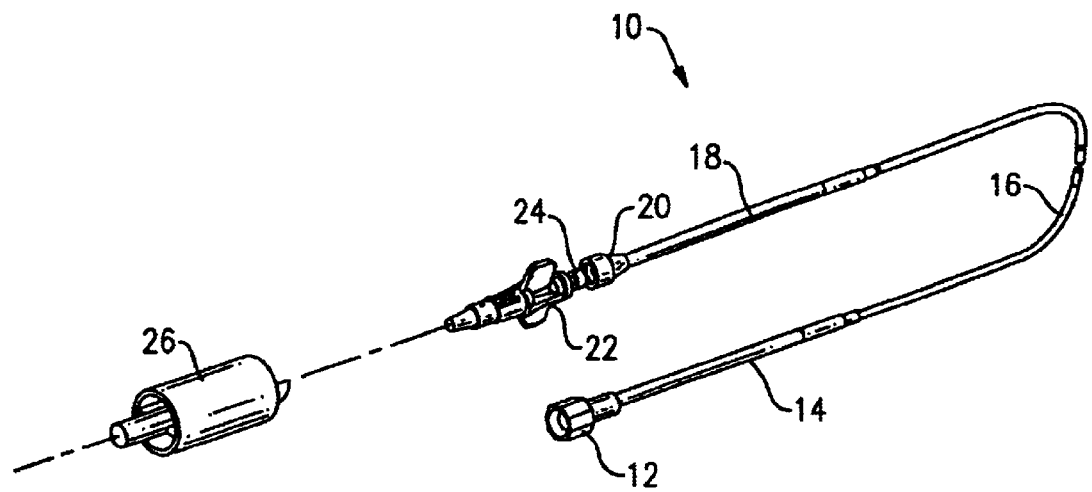
FIG. 1 is an exploded view of the gas sampling system in accordance with a first embodiment of the present invention.

Reference will now be made in detail to the present exemplary embodiments of the invention, examples of which are illustrated in the accompanying drawings. Wherever possible, the same reference numbers will be used throughout the drawings to refer to the same or like parts. An exemplary embodiment of the gas sampling system of the present invention is shown in FIG. 1, and is designated generally throughout by reference numeral 10.

In accordance with the invention, the present invention is directed to a gas sampling system for conducting respiratory gases from a patient respiratory gas output mechanism to a respiratory gas monitoring device. The respiratory gas monitoring device is equipped with a monitor input connector. The gas sampling system includes an input connector configured to couple the gas sampling system to the patient respiratory gas output mechanism. A gas sampling tube is coupled to the input connector. The gas sampling tube is configured to conduct the respiratory gases from the patient to the gas monitoring device. An output connector couples the gas sampling tube to the monitor input connector. An output dryer tube is coupled between the gas sampling tube and the output connector. The output dryer tube is characterized by a tube length and a relative moisture removal efficiency. The relative moisture removal efficiency is dependent on the tube length. The tube length is selected to limit the moisture content of the respiratory gasses being directed into the respiratory gas monitor to a substantially predetermined level. In other words, the output dryer tube removes condensate that forms along the entire length of the gas sampling tube, and depending on the length of the tube, a certain amount of water in the respired gasses is removed before it is directed into either the gas monitor CO2 detector or into a the valve mechanism. In systems that employ valves, the effective operational life-span of the valve mechanism can be extended indefinitely. In fact, the length of the output dryer can be selected to eliminate the need for a valve.

As embodied herein, and depicted in FIG. 1, an exploded view of the gas sampling system 10 in accordance with a first embodiment of the present invention is disclosed. System 10 includes input coupler 12 which is adapted to mate with a tee that connects to a patient respiratory gas output mechanism such as an endotracheal tube or a mask. In one embodiment, input connector 12 is coupled to input dryer tube 14. Input dryer tube 14 is connected to gas sampling tube 16. In another embodiment, dryer tube 14 is not employed, and connector 12 is directly connected to sampling tube 16. Output dryer tube 18 is disposed between gas sampling tube 16 and output connector 20. Output connector 20 is typically connected to a monitor insertion coupler 22, which may include a water trap and gas flow shut-off valve. Shut-off pellet 24 is a component of valve 22, and typically disposed adjacent to output connector 20. The function of shut-off pellet 24 is to close, substantially restricting respiratory gas flow, upon exposure to a predetermined amount of moisture. Shut-off pellet 24 may be implemented as a hydrophilic pellet or a hydrophobic pellet. Depending on the length of output dryer tube 18, monitor insertion coupler 22 need not include the water trap and gas flow shut-off valve. In some applications, plug-in device 22 is coupled to adapter 26, which makes gas sampling system 10 backward compatible with certain gas monitors.

Typically, the useful life of related art gas sampling systems may be in the range of between one or two days. The placement of output dryer tube 18 yields important benefits and advantages. As will be discussed in more detail below, depending on the length of dryer tube 18, all of the condensate formed in gas sampling tube may be removed by dryer tube 18, extending the effective operational life-span of gas sampling system 10 indefinitely. This feature also provides for the elimination of the water trap and gas flow shut-off valve.

Figure 2:
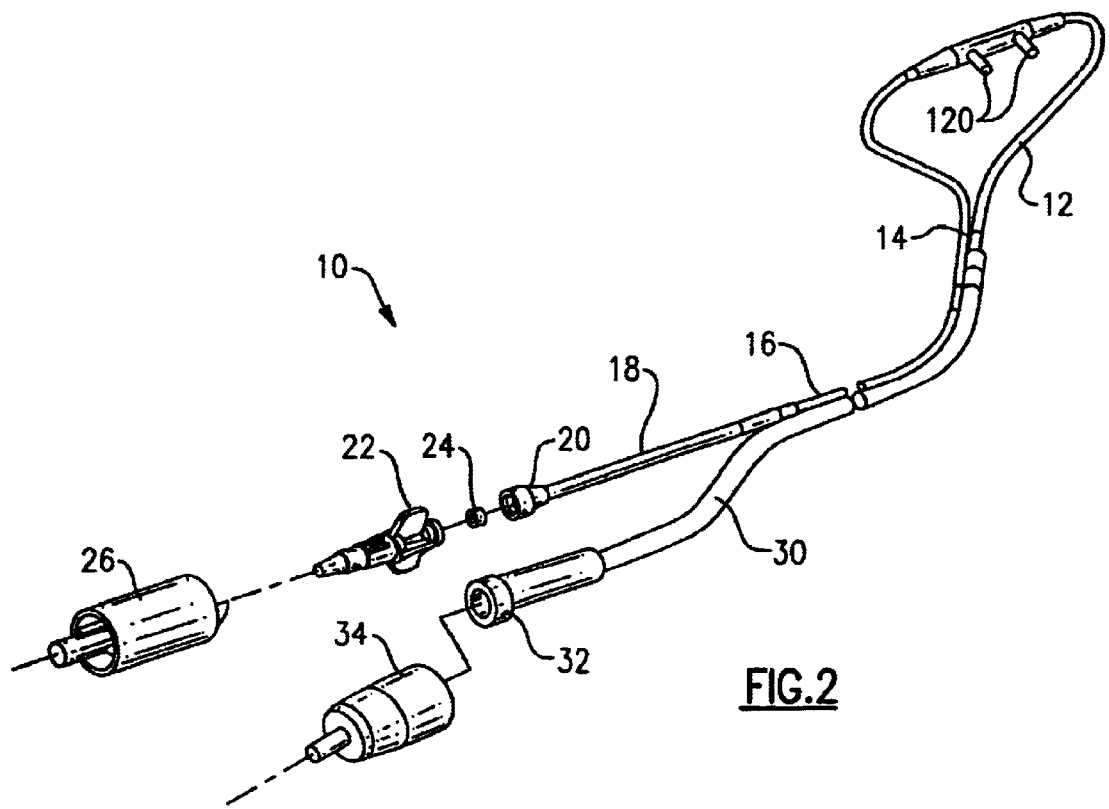
FIG. 2 is an exploded view of the gas sampling system in accordance with a second embodiment of the present invention.

Referring to FIG. 2, an exploded view of gas sampling system 10 in accordance with a second embodiment of the present invention is disclosed. In put connector 14 is coupled to cannula 12, which is equipped with nasal prongs 120. In the embodiment shown, cannula 12 is configured to both sample CO2 and deliver oxygen to a patient. Oxygen delivery tube 30 is coupled to cannula 12 and connector 32. Connector 32 is coupled to oxygen supply adapter 34. In another embodiment, cannula 12 is only configured to sample CO2. Referring back to gas sampling system 10, input connector 14 is connected to gas sampling tube 16, which in this case, is a CO2 sampling line. Output dryer 18 is disposed between sampling tube 16 and output connector 20. In similar fashion to the embodiment depicted in FIG. 1, output connector 20 is typically connected to monitor insertion coupler 22. Monitor insertion coupler 22 allows personnel to conveniently insert sampling system 10 into the gas monitor. Monitor insertion coupler 22 may include a water trap and gas flow shut-off valve. Shut-off pellet 24 is a component of valve, and typically disposed adjacent to output connector 20. The function of shut-off pellet 24 is to close, substantially restricting respiratory gas flow, upon exposure to a predetermined amount of moisture. Shut-off pellet 24 may be implemented as a hydrophilic pellet or a hydrophobic pellet. Depending on the length of output dryer tube 18, monitor insertion coupler 22 need not include the water trap and gas flow shut-off valve. As described above, monitor insertion coupler 22 may, in certain applications, be coupled to adapter 26, which makes gas sampling system 10 backward compatible with certain gas monitors.

Gas sampling tube 16 may be of any suitable type, but there is shown by way of example an extruded plastic tubing. In one embodiment, gas sampling tube 16 a PVC material.

It will be apparent to those of ordinary skill in the pertinent art that modifications and variations can be made to output dryer tube 18 of the present invention depending on cost and complexity issues. For example, output dryer tube 18 may be comprised of Nafionâ tubing that is reinforced mechanically by a braided netting. Nafionâ is a co-polymer that includes tetraflouroethylene (Teflon) and perfluoro-3,6-dioxa-4-methyl-7-octene-sulfonic acid. In short, Nafionâ is a corrosion resistant material that is comprised of Teflon interspersed with sulfonic acid groups. Teflon is hydrophobic. On the other hand, the sulfonic acid groups in Nafionâ are hydrophilic ionic chains extending through the surrounding Teflon matrix. When respiratory gasses propagate in the Nafionâ tubing, water molecules bind to the sulfonic groups disposed on the inside of the tube. The water molecules travel from one sulfonic group to another in the ionic chain until they reach sulfonic groups disposed on the outside wall of the tube. While Nafionâ does not actually include any physical hole, water is conveyed from the inner surface of the tube to the outer surface of the tube by way of the ionic chains. Sometimes, the ionic chains are referred to as ionic pores. It is also important to note that the relative moisture removal efficiency of the output dryer is dependent on the tube length. The tube length can be selected to ensure that water trap and shut-off valve 22 is never exposed to an amount of water in excess of a shut-off amount. In one embodiment, a tube length was selected resulting in an operational life span of approximately 100 hours. In another embodiment, the tube length selected is approximately three inches. The gas sampling system operated indefinitely because substantially all of the moisture borne by the gasses was removed by the output dryer tube.

In other embodiments, output dryer tube 18 may be implemented using microporous filters or molecular sieves. Microporous filters are formed from extrudable plastics that include small pores that are large enough to pass water molecules but are not large enough to allow oxygen (O2), carbon dioxide (CO2), nitrous oxide (N2O), and/or anesthetic agents to pass. On the other hand, the microporous filter may be implemented using a hydrophobic material. In this case, the material allows gasses of all types to pass through it, but the material repels water. A molecular sieve may be used with either the Nafionâ tubing or the microporous filter. The sieve typically surrounds the tubing and is configured to absorb water after it propagates to the outside of the tube. Once the desiccant in the sieve has absorbed a certain amount of water, it is removed. The sieve may be replaced or regenerated. In another embodiment, the molecular sieve operates continuously. This device includes two desiccant chambers. While one chamber is being employed to absorb water, the other chamber is being regenerated.

Those of ordinary skill in the art will recognize that optional input dryer 14 (see FIG. 1) may be implemented using the same materials and design used to implement output dryer 18.

EXAMPLES

The invention will be further clarified by the following examples which are intended to be exemplary of the invention. In the following examples, ME-050 Nafionâ tubing, manufactured by Perma Pure Incorporated, was used to implement the output dryer tube and the input dryer tube. The concept of a relative moisture removal efficiency is illustrated by the following examples. As evidenced by the experimental data presented below, the use of an output dryer proximate to the monitor dramatically increases the effective operation life span of gas sampling system 10.

Example 1

During an initial test, the gas sampling system, as described in FIG. 1, included a 1" input dryer tube 14, a 1" output dryer tube 18, and a water trap and shut-off valve to protect the CO2 detector. The ambient air temperature at the input connector was 40° C. with a relative humidity of 95%. Gas was drawn through the gas sampling system at a rate of 170 mL/minute. Under these conditions, the water shut-off valve closed after approximately two hours of operation. In another experiment, the 1" input dryer tube 14 and the 1" output dryer tube 18 were removed altogether. The water shut-off valve closed after less than one hour of operation. Thus, the gas sampling system employed in these experiments has a relatively low moisture removal efficiency.

Example 2

In a subsequent experiment, the gas sampling system, as described in FIG. 1, was modified to include a 3" input dryer tube 14 and a 3" output dryer tube 18. The ambient air temperature at the input connector was heated to 37° C. with a relative humidity of 95%. Gas was drawn through the gas sampling system at flows ranging from 171 to 178 mL/minute. The test apparatus was allowed to run for approximately 102 hours. The water shut off valve did not close during this period of time. In another experiment, the input dryer tube was modified to include a 2" Nafion tube. The test apparatus ran for over two weeks. The water shut-off valve did not close. The above described gas sampling systems has a high moisture removal efficiency. Those of ordinary skill in the art will recognize that the length of the output dryer tube determines the amount of moisture that will ultimately be directed into the gas monitor. In fact, the above data imply that the use of output dryer tubes greater than 3" in length may eliminate the need for a water shut-off valve altogether.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A gas sampling system for conducting respiratory gases from a patient respiratory gas output mechanism to a respiratory gas monitor, the gas sampling system comprising:
    an input connector configured to couple the gas sampling system to the patient respiratory gas output mechanism;
    a gas sampling tube coupled to the input connector, the gas sampling tube being configured to conduct the respiratory gases;
    an output dryer tubing connected to the gas sampling tube, the output dryer tubing being characterized by a tube length and a relative moisture removal efficiency, the relative moisture removal efficiency being dependent on the tube length, the tube length being selected to limit the moisture content of the respiratory gasses being directed into the respiratory gas monitor to a substantially predetermined level; and
    an output connector coupled to the output dryer tubing, the output connector being configured to couple to the respiratory gas monitor, the output connector including a valve mechanism that closes in response to exposure to a predetermined amount of moisture.

2. The system of claim 1, further comprising an input dryer tube coupled between the input connector and the gas sampling tube, the input dryer tube being characterized by a tube length and a relative moisture removal efficiency, the relative moisture removal efficiency being dependent on the tube length.

3. The system of claim 1, wherein the output connector includes a valve mechanism that closes in response to exposure to a predetermined amount of moisture.

4. The system of claim 3, wherein the tube length is selected to ensure that the valve mechanism is exposed to an amount of moisture below the predetermined amount.

5. The system of claim 3, wherein an effective operational life-span of the gas sampling system ends upon closure of the valve mechanism.

6. The system of claim 5, wherein the tube length is selected to extend the effective operational life-span of the gas sampling system to at least 100 hours.

7. The system of claim 5, wherein the tube length is selected to extend the effective operational life-span of the gas sampling system to greater than 100 hours.

8. The system of claim 3, wherein the valve mechanism includes a shut-off pellet, the shut-off pellet substantially restricting respiratory gas flow upon exposure to the predetermined amount of moisture.

9. The system of claim 8, wherein the shut-off pellet is a hydrophilic pellet.

10. The system of claim 8, wherein the shut-off pellet is a hydrophobic pellet.

11. The system of claim 1, wherein the output dryer tube is comprised of an ionic pore tube dryer.

12. The system of claim 11, wherein the ionic tube dryer is comprised of a co-polymer that includes tetraflouroethylene and perfluoro-3,6-dioxa-4-methyl-7-octene-sulfonic acid.

13. The system of claim 1, wherein the output dryer tube is comprised of a micro-porous tube dryer.

14. The system of claim 1, wherein the output dryer tube is comprised of a molecular sieve dryer.

15. The system of claim 1, wherein the patient respiratory gas output mechanism includes an endotracheal tube.

16. The system of claim 1, wherein the patient respiratory gas output mechanism includes a cannula.

17. The system of claim 16, wherein the cannula is configured to sample CO2.

18. The system of claim 16, wherein the cannula is configured to both sample CO2 and deliver oxygen to a patient.

19. The system of claim 1, wherein the patient respiratory gas output mechanism includes a mask device.

20. The system of claim 1, wherein the patient respiratory gas output mechanism includes a tracheostomy tube.

21. The system of claim 1, wherein the gas sampling tube is comprised of a plastic material.

22. The system of claim 1, wherein the gas sampling tube is comprised of a PVC material.

23. A gas sampling system for conducting respiratory gases from a patient respiratory gas output mechanism to a respiratory gas monitor, the gas sampling system comprising:

an input connector configured to couple the gas sampling system to the patient respiratory gas output mechanism;

a gas sampling tube coupled to the input connector, the gas sampling tube being configured to conduct the respiratory gases;

an output dryer tubing connected to the gas sampling tube, the output dryer tubing receiving unheated and/or non-vaporized respiratory gases from the gas sampling tube, the output dryer tubing being characterized by a tube length and a relative moisture removal efficiency, the relative moisture removal efficiency being dependent on the tube length, the tube length being selected to limit the moisture content of the respiratory gasses being directed into the respiratory gas monitor to a substantially predetermined level;

an output connector coupled to the output dryer tubing, the output connector being configured to couple to the respiratory gas monitor; and wherein the gas sampling system does not include electrically powered components.

* * * * *